(12) United States Patent
Tedeschi et al.

(10) Patent No.: US 6,270,902 B1
(45) Date of Patent: *Aug. 7, 2001

(54) METHOD OF IMPROVING THE ADHERENCE OF CERTAIN CROSSLINKED POLYMER COATINGS CONTAINING PEO OR PVP TO A SUBSTRATE

(75) Inventors: Eugene Tedeschi, Still River, MA (US); Richard Elton, Glen Falls, NY (US); John Hudson, Wells, ME (US)

(73) Assignee: C. R. Bard, Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/838,939

(22) Filed: Apr. 23, 1997

(51) Int. Cl.$^7$ ................................................. B32B 27/40
(52) U.S. Cl. .................. 428/423.1; 427/2.24; 427/2.25; 427/2.28; 427/2.3; 427/2.31; 427/322; 427/407.1; 427/409; 427/533; 427/535; 427/536; 427/551; 428/412; 428/423.3; 428/423.7; 428/423.9; 428/425.5; 428/425.6; 428/425.8
(58) Field of Search ..................... 427/2.24, 2.25, 427/2.28, 2.3, 2.31, 301, 322, 407.1, 409, 533, 535, 536, 551; 428/423.1, 412, 423.3, 423.7, 423.9, 425.5, 425.6, 425.8

(56) References Cited

U.S. PATENT DOCUMENTS

| | | | | |
|---|---|---|---|---|
| 4,459,317 | * | 7/1984 | Lambert | 427/2 |
| 5,001,009 | * | 3/1991 | Whitbourne | 428/412 |
| 5,077,352 | * | 12/1991 | Elton | 525/409 |
| 5,160,790 | * | 11/1992 | Elton | 428/412 |
| 5,662,960 | * | 9/1997 | Hostettler et al. | 427/2.3 |

* cited by examiner

Primary Examiner—D. S. Nakarani
(74) Attorney, Agent, or Firm—Morgan & Finnegan, LLP (57) ABSTRACT

A two step method or process for improving the adherence or bonding of a lubricious coating of a crosslinked polyurethane, polyurea or polyurethaneurea/PEO or PVP coating to a substrate surface, said two step method comprising a first step of subjecting said surface to a surface preparation which results in the treated surface being provided with a functional tie layer containing functional groups for reaction with functional groups of a reaction mixture to be applied in a subsequent second step, which upon curing forms a crosslinked polyurethane, polyurea or polyurethaneurea/PEO or PVP coating and a second step of applying to said tie layer said reaction mixture and curing the reaction mixture. A medical device resulting from the above-described two step method.

18 Claims, 6 Drawing Sheets

METHOD OF IMPROVING THE ADHERENCE OF CERTAIN CROSSLINKED POLYMER COATINGS CONTAINING PEO OR PVP TO A SUBSTRATE

BACKGROUND OF THE INVENTION

It has long been known that hydrophilic coatings with low friction (coefficient of friction of 0.3 or less) are useful for a variety of medical devices such as catheters, catheter introducers, guidewires and the like having an organic substrate or an inorganic substrate. When low friction surfaces are used, the devices, upon introduction into the body, slide easily within arteries, veins, cannula and other body orifices and passageways. There have been a wide variety of methods used to provide the surfaces desired. In some cases the material of the catheter or medical device is formed of a material having good anti-friction properties such as poly(tetrafluoroethylene) or other plastics which tend to avoid abrasion with the body. However, in many cases the selection of materials does not provide the anti-slip properties desired in conjunction with other desirable properties of the particular medical device. In other cases the desired adherence to a particular substrate is not achieved.

The art has recognized that polymer surfaces can be provided with hydrophilic coatings formed by the combinations of certain polymers, both non-cross linked and cross-linked with a hydrophilic polymer like polyvinylpyrrolidone (PVP) or poly(ethylene oxide) (PEO).

For example, U.S. Pat. Nos. 5,077,352, 5,160,790, 5,179,174 and 5,290,585 to ELTON each discloses a flexible, lubricous organic coating formed by applying a mixture of an isocyanate, a polyol, a hydrophilic polymer like poly (ethylene oxide) (PEO) or polyvinylpyrrolidone (PVP) and a carrier liquid to a surface to be coated. The carrier liquid is removed and the mixture reacted to form a lubricous, flexible homogenous coating of crosslinked polyurethane linkages complexed with PVP or PEO particularly suitable for use as a protective lubricous coating on medical devices introduced into the body. For convenience sake the aforementioned crosslinked coatings will be referred to herein as crosslinked polyurethane/PEO coatings (e.g. see U.S. Elton Pat. Nos. 5,077,352 and 5,179,174) and crosslinked polyurethane/PVP coatings (see U.S. Elton Pat. Nos. 5,160,790 and 5,290,585) and the disclosures of the aforementioned patents are incorporated herein by reference.

The use of a crosslinked polyurethane complexed with poly(ethylene oxide) (PEO) or polyvinylpyrrolidone (PVP) has proven to be an effective, lubricous and durable coating on numerous organic substrates. However, there are several organic substrates and numerous inorganic and organometallic substrates (glass, ceramic, metal, silicone, etc.) that first require surface treatment/modification to provide an effective lubricous, durable coating when aforementioned polyurethane complexed with PEO or PVP coatings are applied.

Examples of additional crosslinked polymers complexed with PEO or PVP which provide effective lubricious and durable coatings on various substrates, are those coating compositions disclosed in copending application Ser. No. 08/746,976 filed Nov. 18, 1996 relating to crosslinked polyurea polymers complexed with PEO or PVP coatings as well as coating compositions disclosed in copending application Ser. No. 08/751,405 filed Nov. 18, 1996 relating to crosslinked polyurethaneurea polymers complexed with PEO or PVP.

The disclosure of the aforementioned copending applications are incorporated herein by reference.

The above mentioned crosslinked polyurea/PEO or PVP coatings are formed from the curing of the product resulting from the reaction of an isocyanate and a compound having at least two active hydrogens per molecule selected from the group consisting of polyamines, polymercaptans, and polycarboxylates or compounds with NH, $NH_2$, SH or COOH groups on same molecule, in the presence of the hydrophilic PEO or PVP polymer, with the total sum of the average isocyanate functionality plus the average active hydrogen functionality exceeding 4 and the molar ratio of total NCO groups to total active hydrogens being at least 0.8.

The earlier mentioned crosslinked polyurethaneurea/PEO or PVP coatings are formed from the curing of the product resulting from the reaction of an isocyanate and a polyol in the presence of the PEO or PVP polymer, the stoichiometric ratio of the total NCO groups in the isocyanate to total OH groups in the polyol is such that the resulting polymer formed is a crosslinked polyurethaneurea polymer.

For convenience sake the earlier mentioned crosslinked polyurethane, polyurea or polyurethaneurea polymers complexed with PEO or PVP will be referred to hereinafter as polyurethane, polyurea or polyurethaneurea/PEO or PVP coatings.

An object of this invention is to provide a two step method or process for applying a coating of crosslinked polyurethane, polyurea or polyurethaneurea/PEO or PVP wherein the first step involves providing a substrate with a functional tie layer in such a manner that the treated tie layer surface is rendered more receptive to adhering or bonding with the crosslinked polyurethane, polyurea or polyurethaneurea/PEO or PVP coating resulting from the second step of the two step method of this invention.

Accordingly, an object of this invention is to provide a two step method for improving the adherence or bonding of a crosslinked polyurethane, polyurea or polyurethaneurea/ PEO or PVP to a substrate of a medical device that otherwise would render said coatings not fully suitable as an effective, lubricous, durable coating for said substrate.

A further object of this invention is to provide medical devices whose outer surface is provided with an effective, lubricous and durable coating which resists wear when the coated surface is moved with respect to an adjacent surface. A still further object of this invention is to provide a medical device where inner and/or outer surface exhibits improved lubricity when hydrated with water and/or other aqueous solutions such as blood, urine or other body fluids.

SUMMARY OF THE INVENTION

This invention relates to a two step method for improving the adherence or bonding of a lubricious coating of a crosslinked polyurethane, polyurea or polyurethaneurea complexed with either polyethylene oxide or polyvinylpyrrolidone coatings to a suitable substrate, including several organic substrates and numerous inorganic and organometallic substrates (glass, ceramic, metal, silicone, etc.) that require surface treatment. Of particular interest is improving the adherence of such lubricious coatings to substrates of medical devices.

More particularly, the process of this invention is a two step method wherein the first step involves applying to a surface a functionalized tie layer for improving the adherence to the surface of a lubricious coating resulting from a second step of applying a reaction mixture coating containing functional groups for reaction with functional groups in the tie layer and wherein said coating upon curing forms a crosslinked polyurethane, polyurea or polyurethaneurea/PEO or PVP coating.

In accordance with the method of this invention, the first step provides a means for improving the adherence or bonding of crosslinked polyurethane, polyurea or polyurethaneurea/PEO or PVP coatings to substrates that otherwise might be rendered as unsuitable or at least not completely suitable for such coatings.

More particularly, the invention relates to improved methods and the use of suitable materials to enable the adherence or bonding of an effective lubricous, durable crosslinked polyurethane, polyurea or polyurethaneurea/PEO or PVP coating to be applied to a wide variety of substrates. The methods detailed hereinafter and materials used in such methods involve one or more of the below listed surface preparation techniques for providing the desired functionalized tie layer on which a reaction mixture is applied which upon curing forms a crosslinked polyurethane, polyurea or polyurethaneurea/PEO or PVP coating. The thus coated substrate exhibits improved lubricity when hydrated with water or other aqueous solutions, such as blood, urine or other body fluids. Lubricity results from the ability of the coated surface to imbibe and retain water, providing a lubrication layer of water to reside at the surface of the substrate, so once hydrated, said coatings provide lubricity and durability, and resist wear when the coated surface is moved with respect to an adjacent surface.

The method and materials used in the first step of this invention are of such nature that there are present on the surface resulting from the first step a functionalized tie layer containing functional groups capable of reacting with functional groups (e.g., isocyanate groups, hydroxyl groups, amine groups etc.) present in the subsequently applied coating which upon curing forms a crosslinked polyurethane, polyurea or polyurethaneurea/PEO or PVP lubricious coating.

Among suitable surface preparation techniques and material comprising the first step of the two step method of this invention, the following procedures may be employed, each of which provides a suitable functionalized tie layer that provides functional groups capable of reacting with functional groups in the subsequently applied coating which upon curing forms a crosslinked polyurethane, polyurea or polyurethaneurea/PEO or PVP coating.

1. Application of a suitable primer composition.
2. A high energy surface treatment.
3. Oxidation surface treatment.
4. Multi-layer extrusion.
5. Electrostatic deposition surface treatment.
6. Use of heat activated materials.

Each of the above-mentioned surface treatment procedures will now be discussed under separate heading.

Application of a Suitable Primer Composition

When application of a primer first coating is us as the first step of the two step process of this invention, a substrate is first coated with a suitable primer composition to provide a tie layer and then a second coating of a composition which upon curing forms a crosslinked polyurethane, polyurea or polyurethaneurea complexed with either polyethylene oxide or polyvinylpyrrolidone. The crosslinked polyurethane/PEO or PVP coatings which may be applied in the second step of the process of this invention are disclosed in the earlier mentioned Elton patents and relate to a flexible, lubricous organic coating formed by applying a mixture of an isocyanate, a polyol, a hydrophilic polymer like poly (ethylene oxide) (PEO or polyvinylpyrrolidone (PVP) and a carrier liquid to a surface to be coated. The carrier liquid is removed and the mixture reacted through curing to form a lubricous, flexible homogenous coating of crosslinked polyurethane linkages complexed with PVP or PEO particularly suitable for use as a protective lubricous coating on medical devices introduced into the body. The coatings of the aforementioned patents exhibit a significantly reduced coefficient of friction when exposed to water or aqueous solutions. While they exceptionally adhere to many organic substrates there are some organic substrates which are not acceptable for use with said crosslinked polyurethane/PEO or PVP coatings as well as many inorganic and organometallic substrates (glass, ceramic, metal, silicone, etc.) which the coatings do not normally adhere to in an acceptable manner.

More particularly, it has been found that acceptable adherence of the above-mentioned crosslinked polyurethane/PEO or PVP coatings to substrates that the coatings do not normally adhere to in an acceptable manner can be achieved by employing the two step method or process of this invention wherein in the first step a primer coating is applied to provide a tie layer containing polymers and other materials dissolved or suspended in a solvent that are more easily bonded to the surface than the crosslinked polyurethane/PEO or PVP coatings.

Broadly speaking, the primer composition can be any material which can be deposited on the substrate and which has functional groups reactive with isocyanate or hydroxyl groups present in the crosslinked polyurethane/PEO or PVP coating compositions. Such functional groups would participate in the crosslinking reaction that occurs when a coating is applied and forms a crosslinked polyurea, polyurethaneurea, or polyurethane/PEO or PVP coating. This provides covalent bonding of the coating to the primer.

Examples of suitable materials that can be used in the primer composition which have functional groups reactive with isocyanate or hydroxy groups in the crosslinked polyurethane/PEO or PVP coatings are ethyl vinyl alcohol (EVOH), isocyanate (NCO) terminal prepolymers, polyurethane, epoxies and NCO and OH-functional silanes.

When the lubricious coating is a coating which forms a crosslinked polyurea/PEO or PVP coating upon curing the primer should contain functional groups capable of reacting with functional isocyanate and a compound containing two active hydrogen groups per molecule used in forming the crosslinked polyurea/PEO or PVP coating upon curing.

When the lubricous coating is a coating which forms a crosslinked polyurethaneurea upon curing using the appropriate stoichiometric ratio of total NCO groups in the isocyanate to total OH groups in the polyol, the primer should have appropriate functional groups reactive with the isocyanate or hydroxyl groups in the lubricious coating which forms the crosslinked polyurethaneurea/PEO or PVP coating upon curing.

2. High Energy Treatment

When a high energy treatment is used as the first step of the two step process of this invention, the surface is subjected to a high energy treatment (e.g., plasma, corona and electron discharges) to etch (clean) the surface and make the surface more reactive by (dependent upon plasma reactant gas) depositing functional groups that are reactive with ingredients contained in the crosslinked polyurethane, polyurea or polyurethaneurea/PEO or PVP coatings. Plasma atmospheres which provide reactive functional groups that react with those of the crosslinked polyurethane, polyurea or polyurethaneurea PEO or PVP coatings include, but are not limited to, oxygen, nitrogen, ammonia and hydrogen peroxide. Other chemically inert gases, such as argon or helium may also provide beneficial effects on certain substrates by causing chemical changes to occur on the substrate surface which result in the presence of functional groups after treatment which did not previously exist.

The substrates to be treated may be processed using several of the conventionally available methods, such as:

1. Use of a plasma chamber, whereby parts to be treated are placed in a chamber which is then partially evacuated, and backfilled to an appropriate pressure with the desired atmosphere. High frequency energy is then applied, resulting in a plasma that surrounds all or part of the items.

2. Corona discharge treatment in a suitable atmosphere, such as air, whereby the surface to be treated is brought into close proximity with a high voltage surface containing the corona halo.

3. Other high energy treatments which result in the formation of reactive functional groups or rearrangement of the substrate to produce reactive functional groups, which can react with the PU/PVP or PU/PEO coating.

3. Oxidation Surface Treatment

The first step of the two step process of this invention involves oxidation of a surface, e.g., metal surfaces which upon being oxidized make the surface more receptive to the crosslinked polyurethane, polyurea or polyurethaneurea/PEO or PVP coatings. Prior to applying the coating, the oxidized metal surface may preferably be treated with a primer of the type and in a manner mentioned earlier, such, for example, functional groups which provide surfaces for reaction with the crosslinked polyurethane, polyurea or polyurethaneurea/PEO or PVP coatings.

Alternatively, the oxidized surface may be subsequently treated by conventional chemical means to produce a surface rich in hydroxyl groups. These latter are known to react with the PU/PEO or PU/PVP coatings.

Oxidation may be achieved by one of several means, such as:

1. Thermal treatment of the substrate in the presence of an oxidizing atmosphere such as air, oxygen or peroxide vapor.

2. Chemical treatments of the substrate in an oxidizing solution, such as peroxide solution, a hypochlorite solution or chlorine dioxide solution.

3. Contact of the substrate with a finely divided solid oxidant, such as chrome (VI) oxide.

After one of the above or other oxidation treatments, and other optional chemical processes, the PU/PEO or the PU/PVP coating is applied and cured.

4. Multi Extrusion Two Step Process

The two step process of this invention involves the use of a multi extrusion first step, forming a multi-layer extruded product having an outer layer of material having appropriate functional groups which react with functional groups in the reaction mixture which upon curing forms the crosslinked polyurethane, polyurea or polyurethaneurea/PEO or PVP coatings even though such coatings would not have had an acceptable bonding to the inner layer of the multi-layer of the multi-layer extruded product. Examples of suitable outer layer material are polyurethanes, polyamide Nylons, polyether-polyamide copolymers such as Pebax, polymers having isocyanate (NCO-), amino or OH groups, and anhydrides.

5. Electrostatic Deposition

A two step process of this invention includes using an electrostatic deposition first step of a suitable surface material (e.g., polyamides) to provide a suitable tie layer having functional groups which then are capable of reacting with functional groups of a reaction mixture applied to said tie layer in a second step which upon curing forms a crosslinked polyurethane, polyurea or polyurethaneurea/PEO or PVP coating.

Fusible materials which may be electrically charged by triboelectric, electrostatic or other means and applied by electrostatic deposition and which contain reactive functional groups that react with those in the crosslinked polyurethane, polyurea or polyurethaneurea PEO or PVP coatings are included. Materials which can be finely divided are preferred, for effective charging and application by spraying, fluidized bed dipping or other means of application. Examples of suitable materials include Polyhexamethylene adipate, other high durometer polyurethanes and polyureas. Suitable substrates would include metals, such as stainless steels, nickel titanium alloys (Nitanol), beryllium copper, platinum and other metals and alloys.

6. Heat Activated Materials

A two step process of this invention involves applying to a surface a tie layer heat activated material containing appropriate functional groups (e.g., blocked isocyanates) for reaction with functional groups in a reaction mixture which upon curing forms a crosslinked polyurethane, polyurea or polyurethaneurea/PEO or PVP coating capable of bonding to the tie layer after the heat activated material is exposed to elevated heat conditions.

Suitable heat activated materials useful in the subject application include, but are not limited to, blocked isocyanates and other thermally labile materials which convert to form substances that contain functional reactive groups with the crosslinked polyurethane, polyurea or polyurethaneurea PEP or PVP coatings.

Typically, the surface to be coated would be first coated with a solution of the heat activated material using commercial means such as spraying, dipping, brushing, wiping, etc. After application, the solution is allowed to dry by evaporating the solvent at a suitable temperature. The coated substrate is then subjected to an elevated temperature condition either during the drying process or at a subsequent step, where the thermally labile material undergoes a transition to form a useful primer layer. The PU/PEO or PU/PVP coating is then applied, to adhere to the substrate.

Suitable Medical Device Material

Examples of suitable two step substrate materials (e.g., medical device material) to which the process of this invention may be advantageously employed are as follows:

1. Inorganic Substrates

Examples of inorganic substrates on which the two step process of this invention may be used are metal, glass, ceramic and silicone material.

2. Organic Substrates

Examples of organic substrates on which the two step process of this invention can be carried out are polyethylene, polypropylene, polyether block amide, polyethylene terephthalate, polyetherurethane, polyesterurethane, other polyurethanes, natural rubber, rubber latex, synthetic rubbers, polyester-polyether copolymers, polycarbonates, and other organic materials. Some of these materials are available under the trademarks such as Pebax available from Atochem, Inc. of Glen Rock, N.J. Mylar available from E.I. duPont deNemours and Co. of Wilmington, Del., Texin 985A from Mobay Corporation of Pittsburgh, Pa., Pellethane available from Dow Chemical of Midland, Mich., and Lexan available from General Electric Company of Pittsfield, Mass.

With respect to the lubricious coating applied in the second step after application of the tie layer, the weight ratio of the polyurethane, polyurea or polyurethaneurea polymer matrix to PEO or PVP may be in the range of 0.5 to 15 and preferably between 1 and 3 for most applications.

In addition to components used in forming the coating which becomes a crosslinked polyurethane, polyurea or polyurethaneurea/PEO or PVP on curing other additional additives and modifiers may be included to produce beneficial or desirable effects, as might commonly be employed in coating science. Such additives might include viscosity modifiers, surface active agents, anti-blocking agents, bioactive substances such as antimicrobial agents, pigments, etc.

The coating system applied in the second step is as a solvent solution to a substrate of interest, such as a medical guidewire or catheter. Methods which are commonly practiced in coating technology, such as dipping, spray coating, die wiping, etc. may be employed.

The wet coating is allowed to dry, either under ambient conditions or at elevated temperatures. The reactive ingredients which result in a crosslinked polyurethane, polyurea or polyurethaneurea are then allowed to react in the presence of the PEO or PVP. This cross linking reaction can be carried out at ambient conditions, or preferably at elevated temperature.

The coating composition is essentially uniform throughout. The PEO and PVP is well complexed by the crosslinked polyurethane, polyurea or polyurethaneurea polymer matrix, presumably as a result of the following beneficial effects:

1. The long PEO or PVP chains are physically entrapped in the crosslinked polyurethane, polyurea or polyurethaneurea polymer network.
2. It is also believed that the PEO or PVP molecules are complexed because of the numerous opportunities for hydrogen bonding to occur between the ether oxygens in the PEO or the carboxyl oxygens in the PVP, and the N—H hydrogens formed in the crosslinked polyurethane, polyurea or polyurethaneurea polymer matrix.

The PEO or PVP in these coatings appears to be well complexed and is retained indefinitely even when the coating remains hydrated for extended periods. Prolonged hydration does not result in any significant loss of lubricity or durability. The coatings may also be subjected to repeated cycles of wetting and drying without any loss of properties.

After applying the coating solution, the solvent is preferably allowed to evaporate from the coated substrate by exposure to ambient conditions of from 5 to 120 minutes typically. It is preferable to accomplish this evaporation in such a manner as to minimize the accumulation of water in the uncured coating film resulting from hygroscopic attraction of atmospheric moisture to the PEO or PVP. This can be accomplished readily by minimizing the evaporation time, reducing the ambient humidity, elevating the ambient temperature for drying, or using a combination of these methods.

The coating is subsequently cured. The cure time and temperatures vary with the choice of the reactive ingredients employed and the composition of the substrate. This choice of ingredients also affects the physical properties of the overall coating.

Curing temperatures may range from 75° F. to 350° F. although generally an elevated temperature of 180° to 250° F. is desirable. Cure times may vary from 2 minutes to 72 hours or longer, depending upon the reactive ingredients and the cure temperature. In all cases, the cure conditions are to be non-deleterious to the underlying substrate.

After the coating is cured, it is preferable to rinse or soak the coating in water to remove any uncomplexed PEO or PVP. Generally, a brief rinse of 10 to 15 seconds is sufficient, however, a longer rinse or soak is acceptable since the coating is cured and forms a stable gel when in contact with water. After the rinse, the coating may be dried either at ambient conditions, or at elevated temperatures.

After the coating is formed, the coating can imbibe water from an aqueous solution prior to introduction to the body and can become lubricious. Alternatively, the coating can imbibe water solely from body fluids, even if not introduced to water prior to introduction into the body. It can be dried and remoistened repeatedly and it will retain its lubricating properties. In all cases, the materials are selected so as to be compatible with the body and non-toxic to the body, if the coating is to be used in a body related application as in metallic guidewires, catheters, introducer tubes and the like.

In forming the crosslinked polyurethane, polyurea or polyurethaneurea matrix in accordance with the second step, isocyanates having at least 2 unreacted isocyanate groups per molecule may be used and include but are not limited to polymethylenepolyphenyl isocynate, 4,4'-diphenylmethane diisocyanate and position isomers thereof, 2,4-tolene diisocyanate and position isomers thereof, 3,4-dichlorophenyl diisocyanate and isophorone isocyanate, adducts or prepolymers of isocyanates and polyols such as the adduct of trimethylolpropane and diphenylmethane diisocyanate or toluene diisocyanate. Preferably, an adduct or isocyanate prepolymer, such as that available as Vorite 63 from Caschem Inc., is used. For further examples of polyisocyanates useful in this invention see the ICI Polyurethanes Book, George Woods, published by John Wiley and Sons, New York, N.Y. (1987), incorporated herein by reference.

Polyols used in this invention in obtaining the crosslinked polyurethane or polyurethaneurea polymer matrix can be any of a large number of polyols reactive with the isocyanates to form polyurethanes as known in the art. Examples of suitable polyols include but are not limited to, polyester polyols, polyether polyols, modified polyether polyols, polyester ether polyols, castor oil polyols and polyacrylate castor oil derivatives (triglyceride of 12-hydroxyoleic acid), poly (ethylene adipates), poly (diethyleneglycol) adipates, polycaprolactone diols and polycaprolactone-polyadipate copolymer diols, poly (ethyleneterephthalate) polyols, polycarbonate diols, N,N,N',N-tetrakis (a hydroxypropyl) ethylenediamine, polytetramethylene ether glycol, ethyleneoxide adducts of polyisopropylene diols, ethylene oxide adducts of polyisopropylene triols. Trademark products include Desmophen, 651A-65, 1300 75 and 800 available from Bayer Corporation of Pittsburgh, Pa., Niax E-59 and others available from Union Carbide in Danbury, Conn., Desmophen-550 DU, -1600U, -1920D, and -1150 available from Bayer, and DB oil, Polycin- 12, Polycin 55 and Polycin 99F available from CasChem, Inc. of Bayonne, N.J., as well as Desmophen A450, A365 and A160 available from Bayer are useful. Many other polyols are available and can be used as known to those skilled in the art.

Preferred active hydrogen species used in forming a crosslinked polyurea coating upon curing in accordance with the second step of this invention include triethyleneglycoldiamine available as Jeffamine EDR-148(Texaco Chemical, Bellaire, Tex.); polyetherdiamines such as Jeffamine ED-600, Jeffamine ED-900 and Jeffamine ED-2001 (Texaco Chemical); polyethertriamines such as Jeffamine T-403; urea condensates of polyetheramines such as Jeffamine DU-700; and amine terminated polypropyleneglycols such as Jeffamine D-400 and Jeffamine D-2000.

Heterocyclic diamines and amine adducts of the same may work well in some applications, such as products YSE-CURE F-100, B-002, and N-002 (available from Ajinomoto, USA, Teanick, N.J.). Also useful are urethane modified melamine polyols containing both amine and hydroxyl groups, available as Cylink HPC (Lytec Industries, West Patterson, N.J.).

Examples of useful polysulfides containing 2 or more SH groups per molecule include polymers of bis-(ethylene oxy) methane containing disulfide linkages, such as LP-3, LP-32, and LP-33 available from Morton Thiokol Corporation.

The (PEO) poly(ethylene oxide) useful in accordance with this invention preferably has a mean molecular weight of from about 50,000 to 5,000,000.

The (PVP) polyvinylpyrrolidone used in accordance with the present invention preferably has a number average molecular weight of from about 50,000 to 2.5 million. PVP having a number average molecular weight of about 360,000 is preferred. Examples of polyvinylpyrrolidone materials useful in this invention are those available from BASF Corp., Parsippany, N.J. as Kollidon 90, Luviskol K90, Luviskol K80 and Luviskol K60, and those available from GAF Corporation, as Plasdone 90, PVP K90 and PVP K120.

Commercially available polyvinylpyrrolidone products usually contain approximately 3–5% (w/w) water. Furthermore, polyvinylpyrrolidone is very hygroscopic, and tends to accumulate water on normal storage when exposed to air. Since water is very reactive toward isocyanates, it is preferred, but not essential, to reduce the water content to less than 0.5% prior to use in preparing coating formulations. This may be readily accomplished by vacuum drying an appropriate quantity of polyvinylpyrrolidone, for example, by heating it for eighteen hours at 200° F., while maintaining a vacuum of at least 6 inches of mercury.

The solvents used are those that do not react with the isocyanate, the polyol or active hydrogen containing compound or the polyethylene oxide or polyvinylpyrrolidone but are solvents for the reactants in step 2. The solvents should be free of reactive groups such, for example as hydroxyl, amine, polyol or sulfhydryl. The solvent must further be capable of dissolving the isocyanate, active hydrogen containing compound and poly(ethylene oxide) or polyvinylpyrrolidone. Preferred solvents available commercially in a suitably dry form include but are not limited to methylene chloride, dibromomethane, chloroform, dichloroethane, and dichloroethylene. When methylene chloride is used, the solids content of the coating solution may be 0.3 to 15% (w/w) and preferably 2.25 to 4% (w/w). When dibromomethane is used, the solids content of the coating solution may be 0.4 to 10% (w/w) and preferably 1.2 to 2.5% (w/w). Other solvents meeting the above objectives are also suitable.

Viscosity and flow control agents may be used to adjust the viscosity and thixotropy to a desired level. Preferably the viscosity is such that the coating can be formed on the substrate at the desired thickness. Viscosities of from 50 to 500 cps can be used although higher or lower viscosities may be useful in certain instances. Viscosity control agents include but are not limited to fumed silica, cellulose acetate butyrate and ethyl acrylate/2-ethyl hexyl acrylate copolymer. Flow control agents are preferably used in amounts from 0.05 to 5 percent by weight of coating.

Antioxidants are used to improve oxidative stability of the cured coatings and include but are not limited to tris (3,5-di-t-butyl-4-hydroxy benzyl) isocyanurate, 2,2'-methylenebis (4-methyl-6-t-butyl phenol), 1,3,5-Trimethyl-2,4,6-tris (3,5-di-t-butyl-4-hydroxybenzyl) benzene, butyl hydroxy toluene, octadecyl 3,5, di-t-butyl-4-hydroxyphdrocinnamate, 4,4 methylenebis (2,6-di-t-butylphenol), p,p-dioctyl diphenylamine, 1,1,3-tris-(2-methyl-4-hydroxy-5-t-butylphenyl) butane. Antioxidants are preferably used in amounts from 0.01 to 1 percent by weight of coating.

Conventional pigments can be added to impart color or radiopacity, or to improve appearance of the coatings.

Air release agents or defoamers include but are not limited to polydimethyl siloxanes, 2,4,7,9-tetramethyl-5-decyn-4,7-diol, 2-ethylhexyl alcohol, n-beta-aminoethyl-gamma-aminopropyl-trimethoxysilane. Air release agents are often used in amounts from 0.0005 to 0.5 percent by weight of coating.

The organic substrates that can be coated with the coatings of this invention using PEO or PVP as the hydrophilic polymer include polyether block amide, polyethylene terephthalate, polyetherurethane, polyesterurethane, other polyurethanes, natural rubber, rubber latex, synthetic rubbers, polyester-polyether copolymers, polycarbonates, and other organic materials. Some of these materials are available under the trademarks such as Pebax available from Atochem, Inc. of Glen Rock, N.J., Mylar available from E.I. duPont deNemours and Co. of Wilmington, Del., Texin 985A from Bayer Corporation of Pittsburgh, Pa., Pellethane available from Dow Chemical of Midland, Mich., and Lexan available from General Electric Company of Pittsfield, Mass.

The following are specific examples of the two step process of this invention employing a first step to produce a functionalized tie layer followed by a second step of applying a reaction mixture which upon curing forms a crosslinked polyurethane, polyurea or polyurethaneurea/ PEO or PVP.

EXAMPLE 1

A crosslinked polyurethane/PEO coating formulation was prepared by weighing the following components into a disposable plastic container:

a) 1.17 grams of a polyfunctional polyol available as Polycin 12 (Caschem Inc.);
b) 3.0 grams of a 60% solution of a trimethylolpropane-toluene diisocyanate adduct in PMA solvent available as Mondur CB-60N (Bayer Corp.);
c) 100 grams of a 3.3% solution of poly(ethylene oxide) mean molecular weight 300,000 available as Polyox WSR-N750 (Union Carbide Corp.);
d) 104 grams of methylene chloride.

A functional polymer solution was prepared by dissolving 4.0 grams of an ethylene acrylic acid copolymer, available as Primacor 5990 (Dow Chemical Corp.) in 96.0 grams of cyclopentanone using mild heating to effect solution.

A length of stainless steel wire approximately 0.016 inches in diameter was dipped into the Primacor solution during 90 seconds. It was then allowed to air dry for approximately 20 minutes, followed by baking at 200° F. for 30 minutes. Following this the coated wire was dipped in the crosslinked polyurethane/PEO coating solution as above, air dried for 20 minutes, and baked for 60 minutes at 200° F. to effect the cure of the coating.

The resulting product was a wire with a flexible adherent coating that when wetted with water became noticeably lubricious. Repeated rubbing of the wire under running water with moderate finger pressure did not reduce the coating lubricity appreciably.

EXAMPLE 2

A crosslinked polyurea/PEO coating formulation was prepared by weighing the following components into a disposable plastic container.
a) 1.09 grams of a polyfunctional amine available as Jeffamine ED-600 (Texaco Chemical Co.);
b) 4.36 grams of a 60% solution of a trimethylolpropane-toluene diisocyanate adduct in PMA solvent available as Mondur CB-60N (Bayer Corp.);
c) 75.0 grams of a 3.3% solution of poly(ethylene oxide) mean, molecular weight 300,000 available as Polyox WSR-N750 (Union Carbide Corp.) in
d) 75 grams of methylene benzoate.

A functional polymer solution was prepared by dissolving 5.0 grams of an ethylene acrylic acid copolymer available as Primacor 5990 (Dow Chemical Corp.) in 95.0 grams of 4/1 xylene/isopropanol blend using mild heating to effect solution.

A length of nickel/titanium wire (Nitinol) approximately 0.020 inches in diameter was dipped into the Primacor solution during 90 seconds. It was then allowed to air dry approximately 20 minutes, followed by baking at 200° F. for 30 minutes. Following this the coated wire was dipped in the crosslinked polyurea/PEO coating solution as above, air dried for 20 minutes, and baked for 60 minutes at 200° F. to effect the cure of the coating.

The resulting product was a wire with a flexible adherent coating that when wetted with water became noticeably lubricious. Repeated rubbing of the wire under running water with moderate finger pressure did not reduce the coating lubricity appreciably.

EXAMPLE 3

A crosslinked polyurea/PEO coating solution as in Example 2 was prepared.

A functionalized polyurethane solution was prepared by combining the following components into a disposable plastic container.
a) 5.6 grams of a polyfunctional polyol available as Polycin 12 (Caschem Inc.);
b) 14.4 grams of a 60% solution of a trimethylolpropane-toluene diisocyanate adduct in PMA solvent available as Mondur CB-60N (Bayer Corp.);
c) 74.6 grams of methylene chloride.

A length of nickel/titanium wire (Nitinol) approximately 0.020 inches in diameter was dipped into the polyurethane solution during 90 seconds. It was then allowed to air dry for approximately 20 minutes, followed by baking at 200° F. for 60 minutes. Following this the coated wire was dipped in the crosslinked polyurea/PEO coating solution as above, air dried for 20 minutes, and baked for 60 minutes at 200° F. to effect the cure of the coating.

The resulting product was a wire with a flexible adherent coating that when wetted with water became noticeably lubricious. Repeated rubbing of the wire under running water with moderate finger pressure did not reduce the coating lubricity appreciably.

EXAMPLE 4

A crosslinked polyurethane/PEO coating solution as in Example 1 was prepared.

A functionalized polymer solution was prepared by dissolving 10.0 grams of a ethylene acrylic acid copolymer available as Primacor 5990 (Dow Chemical Corp.) in 90.0 grams of a 9/1 toluene/isopropanol blend using mild heating to effect solution.

A length of polyethylene tubing approximately 0.035 inches in diameter was dipped into the Primacor solution during 90 seconds. It was then allowed to air dry for approximately 20 minutes, followed by baking at 200° F. for 30 minutes. Following this the coated tube was dipped in the crosslinked polyurethane coating solution as above, air dried for 20 minutes, and baked for 60 minutes at 200° F. to effect the cure of the coating.

The resulting product was a tubing with a flexible adherent coating that when wetted with water became extremely lubricious. Repeated rubbing of the tubing under running water with moderate finger pressure did not reduce the coating lubricity appreciably.

Polyethylene is a substrate which is normally difficult to coat with crosslinked polyurethane/PEO coatings alone. For comparison, the same tubing was coated with only the coating, without the functional ethylene acrylic acid copolymer. The result was a tubing which initially became slippery when wetted with water, but which lost lubricity when rubbed due to loss of adhesion of the wet coating to the polyethylene.

EXAMPLE 5

A crosslinked polyurethane/PEO coating solution as in Example 1 was prepared.

A stainless steel wire, approximately 0.016 inches in diameter was coated with nylon 6 using an electrostatic deposition process whereby the nylon 6 was fused to the wire to form an adherent layer with reactive functional groups.

A length of this coated wire was dipped into the crosslinked polyurethane/PEO coating solution. It was then allowed to air dry approximately 20 minutes, followed by baking at 200° F. for 60 minutes.

The resulting product was a wire with a flexible adherent coating that when wetted with water became extremely lubricious. Repeated rubbing of the wire under running water with moderate finger pressure did not reduce the coating lubricity Stainless steel is a substrate which normally difficult to coat with crosslinked polyurethane/PEO coatings alone. For comparison, the same wire, was coated with only crosslinked polyurethane/PEO coating, without the functional nylon 6 polymer. The result was a wire which initially became slippery when wetted with water but which lost lubricity when rubbed due to loss of adhesion of the wet coating to the stainless steel.

EXAMPLE 6

A polyurethaneurea/PEO coating formulation was prepared by weighing the following components into a disposable plastic container:
 a) 1.17 grams of a polyfunctional polyol available as Polycin 12 (Caschem Inc.);
 b) 4.65 grams of a 60% solution of trimethylol propane-toluene diisocyanate adduct in PMA solvent, available as Mondur CB-60N (Bayer Corp.);
 c) 133 grams of a 3.3% solution of poly(ethylene oxide) mean molecular weight 300,000 available as Polyox WSR-N750 (Union Carbide Corp) in methylene chloride
 d) 145 grams of methylene chloride.

A solution of a functionalized polymer was prepared by dissolving an ethylene-acrylic acid copolymer available as Primacor 5990 (Dow Chemical Corp.) in cyclopentanone to a concentration of 4% using mild heating to effect solution.

A coiled length of fine stainless steel wire approximately 0.024 inches in diameter was dipped into the Primacor solution during 90 seconds. It was then allowed to air dry for approximately 30 minutes, followed by a bake at 200° F. for 30 minutes. Following this the coated coiled wire was dipped in the polyurethaneurea/PEO coating, air dried 20 minutes and baked for 60 minutes at 200° F. to effect the cure of the coating.

The resulting product was a coiled wire assembly with a flexible adherent coating that when wetted with water became noticeably lubricious. Repeated rubbing of the coiled wire under running water with moderate finger pressure did not reduce the coating lubricity appreciably.

Figure 1:
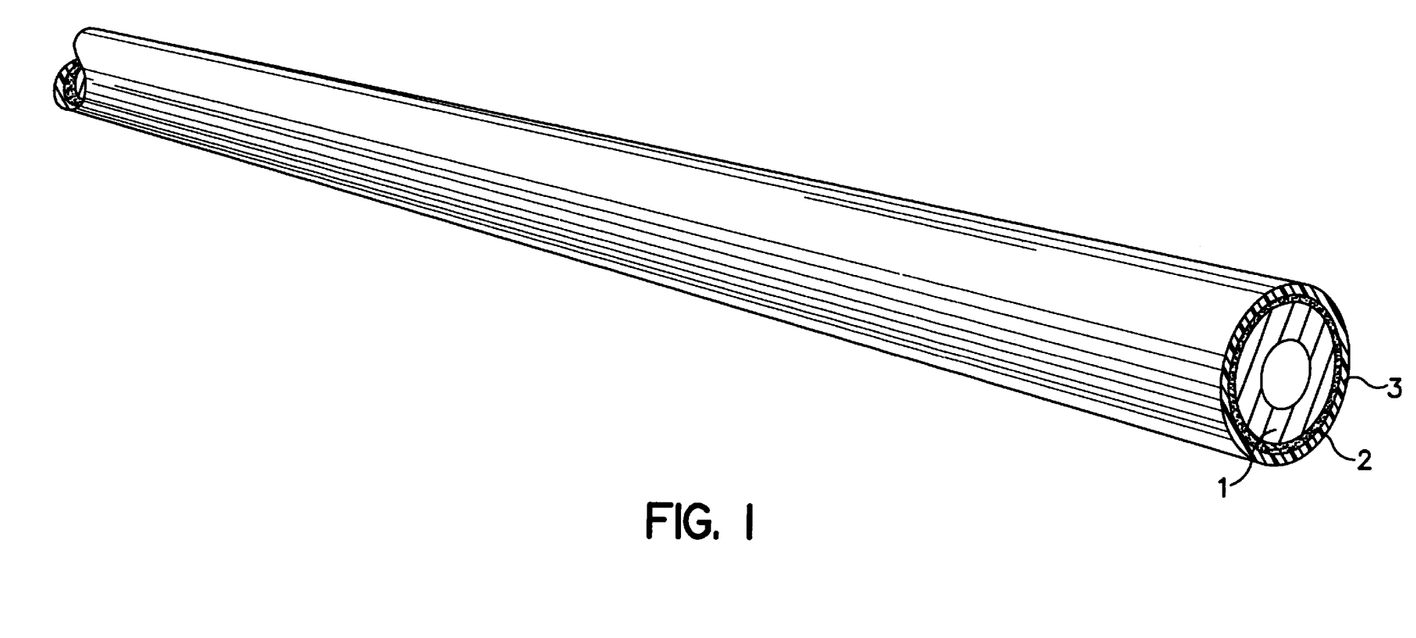
FIG. 1 is a perspective view of a medical metallic tubing containing a lubricious coating formed in accordance with this invention in which adherence of a lubricious coating of a crosslinked polyurethane, polyurea or polyurethaneurea/ PEO or PVP to an outer surface of said medical tubing is enhanced by providing a functionalized tie layer on the outer surface of said tubing on which a reaction mixture is applied and subsequently cured to form said lubricious coating of a crosslinked polyurethane, polyurea or polyurethaneurea/ PEO or PVP coating.
Figure 2:
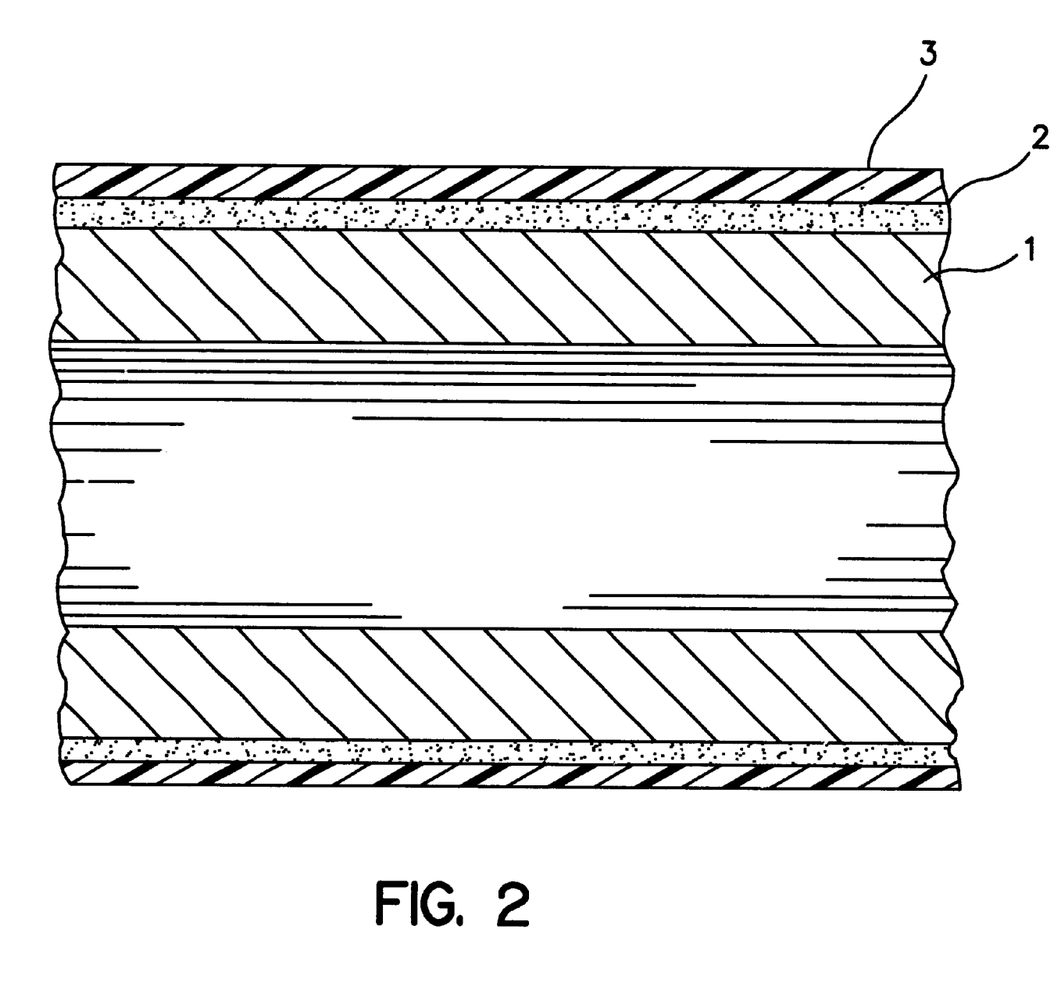
FIG. 2 is a cross-sectional view of a length of the coated tubing of FIG. 1.

Referring now to FIG. 1 and FIG. 2 there is shown a medical metallic tubing 1 having a functionalized tie layer 2 on which is coated a crosslinked polyurethane, polyurea or polyurethaneurea/PEO or PVP coating 3 produced in accordance with the two step method of this invention.

Figure 3:
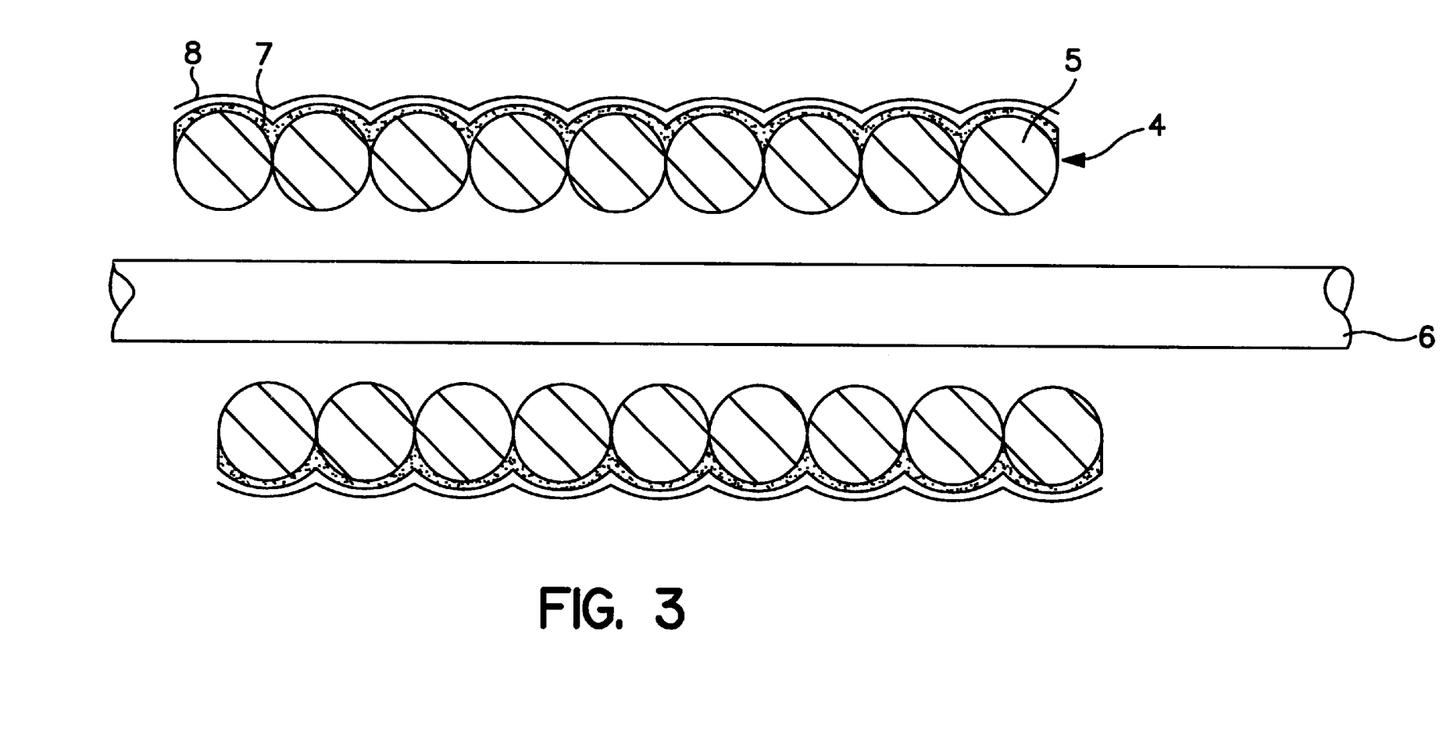
FIG. 3 is a cross-sectional view of the body of a spring guidewire comprising a stainless steel or other metallic winding wire through which a core wire passes, said winding wire having coated thereon a functionalized tie layer on which is coated a reaction mixture which upon curing provides a lubricious crosslinked polyurethane, polyurea or polyurethaneurea/PEO or PVP coating.

FIG. 3 illustrates a cross-section view of a medical spring guidewire 4 comprising a stainless steel or other metallic winding wire 5 through which metallic core wire 6 passes, said winding wire 5 being provided on its outer surface a functionalized tie layer 7 over which is applied a crosslinked polyurethane, polyurea or polyurethaneurea/PEO or PVP coating 8 in accordance with the two step method of this invention.

Figure 4:
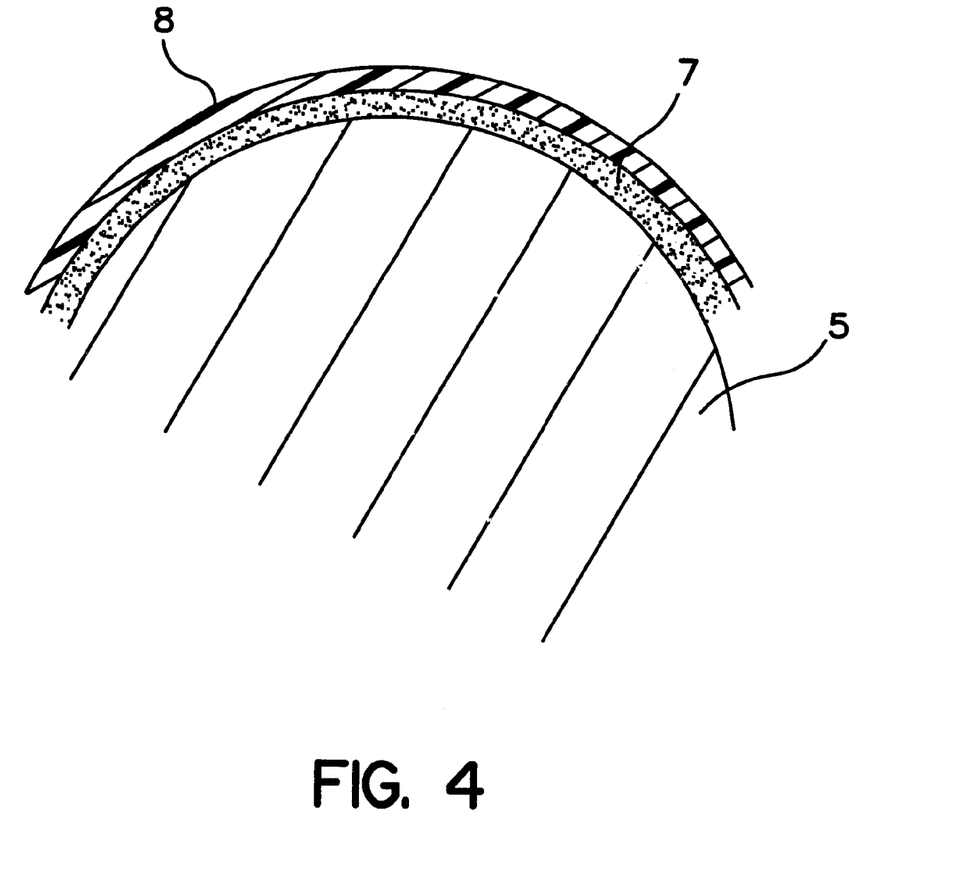
FIG. 4 is an enlarged cross-sectional view of an interface of a segment of the winding wire, functionalized tie layer and lubricious coating shown in FIG. 3.

As shown in FIG. 4, which is an enlarged cross-sectional view of a segment of the winding wire 5 of FIG. 3, there is provided on its outer surface the tie layer 7 on which is coated a lubricious crosslinked polyurethane, polyurea or polyurethaneurea/PEO or PVP coating 8.

Figure 5:
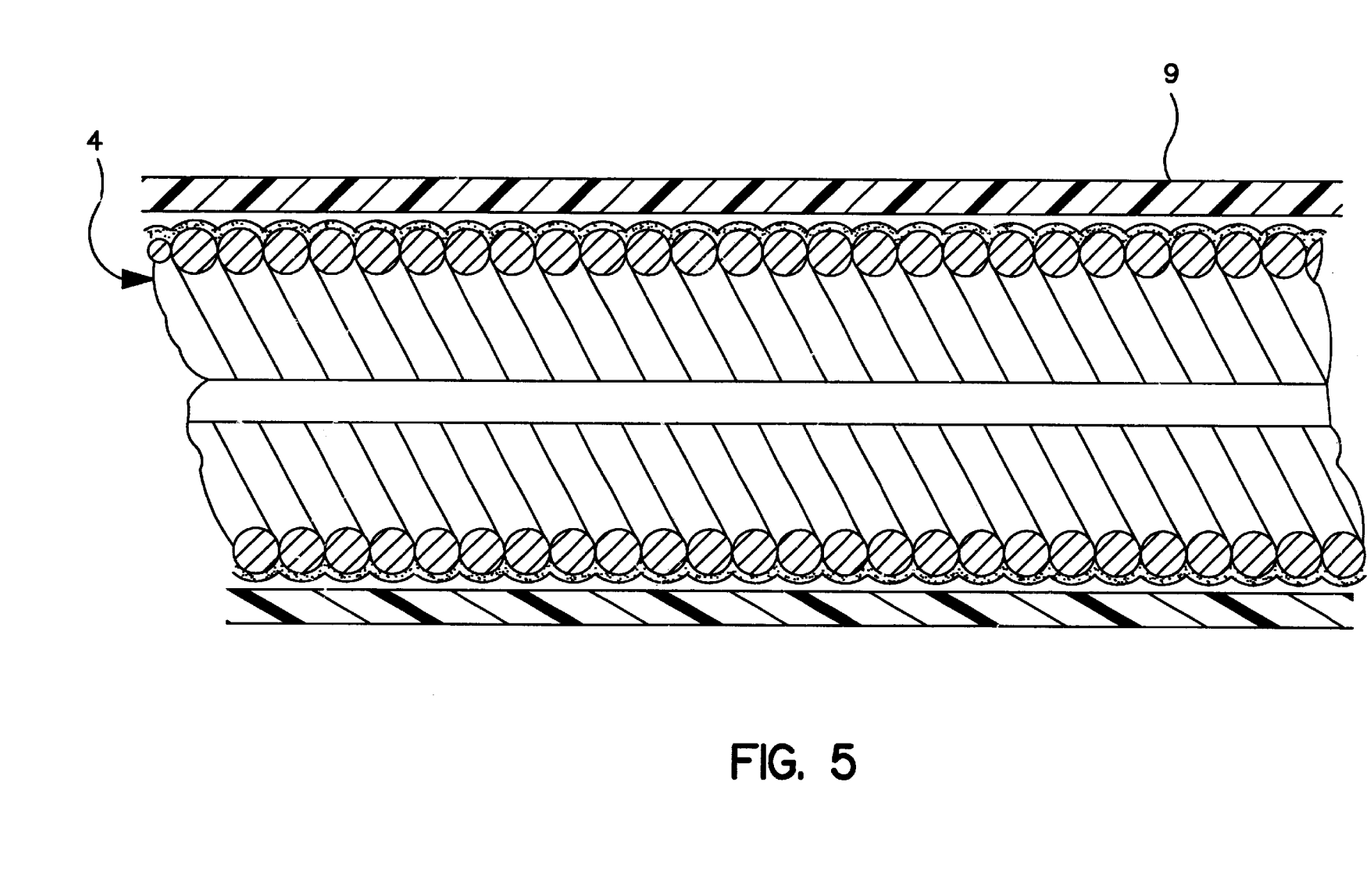
FIG. 5 is a cross-sectional view of a section of catheter tubing into which the lubricious coating steel guidewire shown in FIGS. 3 and 4 is inserted.

As shown in FIG. 5, there is provided a catheter tubing 9 into which passes the coated guidewire 4 shown in FIGS. 3 and 4.

Figure 6:
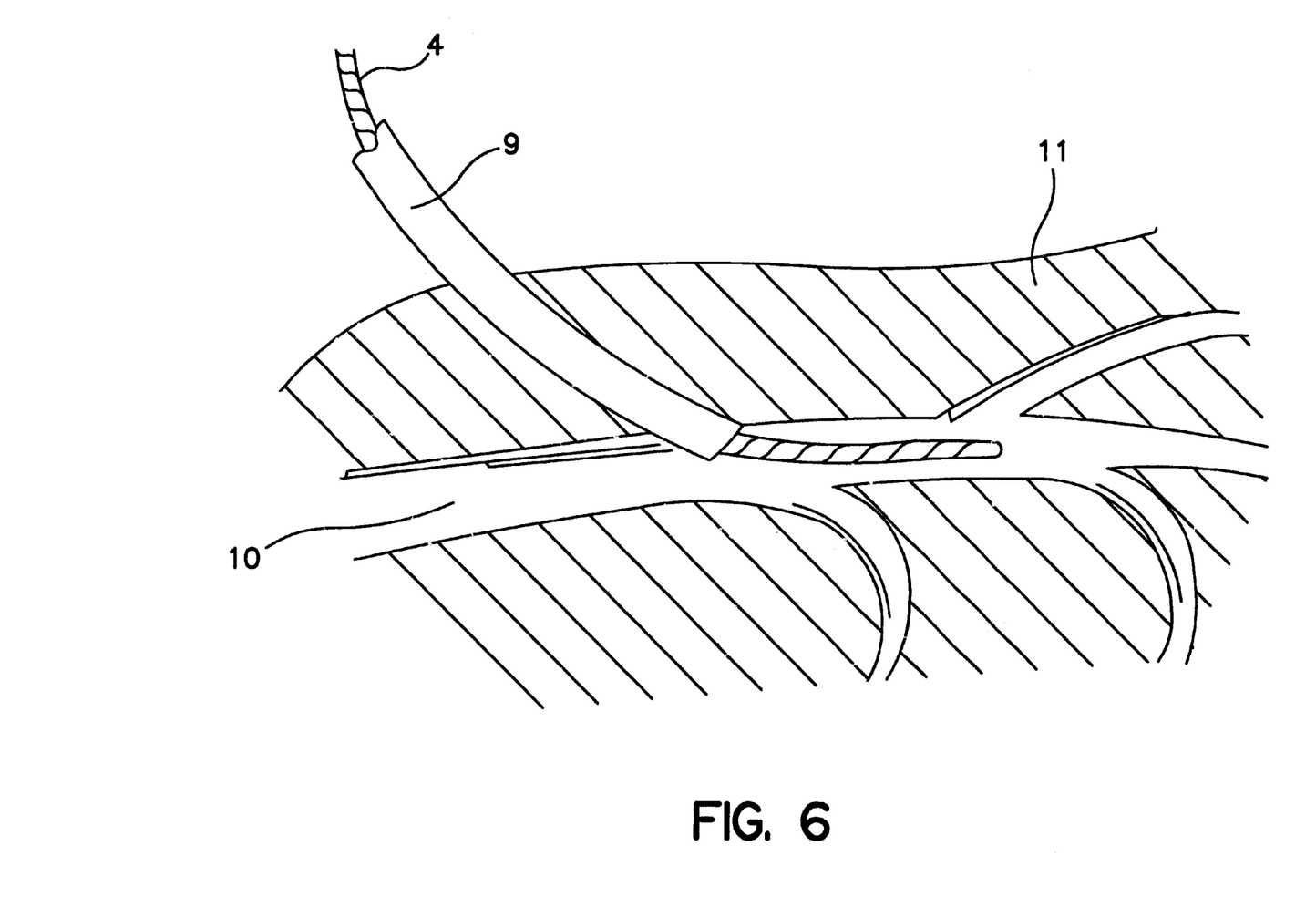
FIG. 6 is a perspective view of the guidewire and catheter shown in FIG. 5 in a blood vessel with the catheter being shown advancing over the guidewire.

As shown in FIG. 6, the catheter 9 of FIG. 5 is shown advancing over the guidewire 4 of FIGS. 3 and 4 located in lumen 10 of blood vessel 11.

Changes in construction will occur to those skilled in the art and various apparently different modifications and embodiments may be made without departing from the scope of the invention. The matter set forth in the foregoing description and accompanying drawings is offered by way of illustration only. The actual scope of the invention is intended to be defined in the following claims when viewed in their proper perspective against the prior art.

What is claimed is:

1. A two step method or process for improving the adherence or bonding of a lubricious coating of a crosslinked polyurethane, polyurea or polyurethaneurea/PEO or PVP coating to a substrate surface, said two step method comprising a first step of subjecting said surface to a surface preparation which results in the treated surface being provided with a functional tie layer containing functional groups capable of forming covalent bonds with functional groups of a reaction mixture to be applied in a subsequent second step, which reaction mixture comprises a molecule having at least two unreacted isocyanate groups per molecule and PEO or PVP and which reaction mixture upon curing forms a crosslinked polyurethane, polyurea or polyurethaneurea/PEO or PVP coating and a second step of applying to said tie layer said reaction mixture, forming a covalent bond between said tie layer and said reaction mixture and curing the reaction mixture.

2. A two step method according to claim 1 wherein the surface preparation first step is chosen to provide the desired functional tie layer, selected from the group consisting of (1) an application of a suitable primer composition containing appropriate functional groups, (2) a high energy surface treatment which provides suitable functional groups, (3) an oxidation surface treatment which provides appropriate functional groups, (4) multi-layer extrusion which provides appropriate functional group, (5) an electrostatic deposition surface treatment which provides appropriate functional group and (6) use of heat activatable material providing appropriate functional groups.

3. A two step method according to claim 1 wherein the surface preparation step is an application of a suitable primer composition to said substrate.

4. A two step method according to claim 1 wherein the surface preparation step is an application of a suitable high energy surface treatment to said substrate.

5. A two step method according to claim 1 wherein the surface preparation step is an application of a suitable oxidation surface treatment to said substrate.

6. A two step method according to claim 1 wherein the surface preparation step is an application of a suitable multi-layer extrusion to said substrate.

7. A two step method according to claim 1 wherein the surface preparation step is an application of a suitable electrostatic deposition surface treatment to said substrate.

8. A two step method according to claim 1 wherein the surface preparation step is an application of a suitable heat activatable material to said substrate.

9. A two step method according to claim 1 wherein the lubricious coating that is formed upon curing is a crosslinked polyurethane/PEO or PVP coating.

10. A two step method according to claim 1 wherein the lubricious coating that is formed upon curing is a crosslinked polyurea/PEO or PVP coating.

11. A two step method according to claim 1 wherein the lubricious coating that is formed upon curing is a crosslinked polyurethaneurea/PEO or PVP coating.

12. The two step method or process for improving the adherence or bonding of a lubricous coating according to claim 1, wherein the functional tie layer is covalently bound to the substrate surface.

13. The method according to claim 1, wherein the lubricious coating formed by the reaction mixture has a weight ratio of the polyurethane, polyurea or polyurethaneurea to PEO or PVP in the range of 0.5 to 15.

14. A medical device having on its outer surface a functionalized tie layer for improving the adherence thereto of a lubricious coating of a crosslinked polyurethane, polyurea or polyurethaneurea/PEO or PVP coating, said functionalized tie layer having functional groups for reaction with functional groups of a reaction mixture when applied thereto and which reaction mixture comprises a molecule having at least two unreacted isocyanate groups per molecule and PEO or PVP and which reaction mixture upon curing forms a crosslinked polyurethane, polyurea or polyurethaneurea/PEO or PVP.

15. A medical device according to claim 14 wherein the lubricious coating that is formed upon curing is a crosslinked polyurethane/PEO or PVP coating.

16. A medical device according to claim 14 wherein the lubricious coating that is formed upon curing is a crosslinked polyurea/PEO or PVP coating.

17. A medical device according to claim 14 wherein the lubricious coating that is formed upon curing is a crosslinked polyurethaneurea/PEO or PVP coating.

18. The medical device according to claim 12, wherein the lubricious coating formed by the reaction mixture has a weight ratio of the polyurethane, polyurea or polyurethaneurea to PEO or PVP in the range of 0.5 to 15.

* * * * *